(12) United States Patent
Kawamura et al.

(10) Patent No.: US 9,168,232 B2
(45) Date of Patent: Oct. 27, 2015

(54) TRANSDERMALLY ABSORBABLE PREPARATION

(75) Inventors: Naohisa Kawamura, Kasukabe (JP); Chie Sugaya, Kasukabe (JP)

(73) Assignee: NIPRO PATCH CO., LTD. (JP)

( * ) Notice: Subject to any disclaimer, the term of this patent is extended or adjusted under 35 U.S.C. 154(b) by 0 days.

(21) Appl. No.: 13/394,656

(22) PCT Filed: Sep. 1, 2010

(86) PCT No.: PCT/JP2010/064937
§ 371 (c)(1),
(2), (4) Date: Apr. 30, 2012

(87) PCT Pub. No.: WO2011/027786
PCT Pub. Date: Mar. 10, 2011

(65) Prior Publication Data
US 2012/0226245 A1 Sep. 6, 2012

(30) Foreign Application Priority Data
Sep. 7, 2009 (JP) ................................. 2009-206183

(51) Int. Cl.
A61M 35/00 (2006.01)
A61K 9/70 (2006.01)
A61K 31/167 (2006.01)
A61K 31/465 (2006.01)
A61F 13/02 (2006.01)

(52) U.S. Cl.
CPC ............. *A61K 9/7061* (2013.01); *A61K 9/7069* (2013.01); *A61K 31/167* (2013.01); *A61K 31/465* (2013.01); *A61M 35/00* (2013.01); *A61F 13/02* (2013.01); *A61F 13/0246* (2013.01); *A61F 13/0253* (2013.01)

(58) Field of Classification Search
CPC ...... A61M 35/00; A61F 13/02; A61F 13/023; A61F 13/0236; A61F 13/0246; A61F 13/0253; A61K 9/7061; A61K 9/7069; A61K 31/167; A61K 31/465
USPC .................. 604/307, 308; 602/48, 50, 51, 52; 424/424, 444, 447, 449
See application file for complete search history.

(56) References Cited

U.S. PATENT DOCUMENTS

| | | | | | |
|---|---|---|---|---|---|
| 3,387,001 | A | * | 6/1968 | Hargrove | 540/478 |
| 4,166,810 | A | * | 9/1979 | Cullinan et al. | 540/478 |
| 4,322,351 | A | * | 3/1982 | Miller et al. | 514/183 |
| 4,667,030 | A | * | 5/1987 | Cullinan | 540/478 |
| 4,675,400 | A | * | 6/1987 | Cullinan | 540/478 |
| 4,751,087 | A | * | 6/1988 | Wick | 424/449 |
| 4,801,688 | A | * | 1/1989 | Laguzza et al. | 530/391.9 |
| 4,908,213 | A | | 3/1990 | Govil et al. | |
| 5,043,336 | A | * | 8/1991 | Cullinan | 514/218 |
| 5,043,340 | A | * | 8/1991 | Cullinan | 514/283 |
| 5,435,879 | A | * | 7/1995 | Knutson et al. | 156/327 |
| 5,962,012 | A | * | 10/1999 | Lin et al. | 424/448 |
| 6,284,269 | B1 | * | 9/2001 | Struengmann et al. | 424/461 |
| 6,617,387 | B2 | * | 9/2003 | Dreher et al. | 524/510 |
| 7,875,612 | B2 | * | 1/2011 | Green et al. | 514/243 |
| 8,044,200 | B2 | * | 10/2011 | Xu et al. | 544/258 |
| 8,105,568 | B2 | * | 1/2012 | Vlahov et al. | 424/1.73 |
| 8,288,557 | B2 | * | 10/2012 | Vlahov et al. | 546/290 |
| 8,465,724 | B2 | * | 6/2013 | Vlahov et al. | 424/1.53 |
| 2003/0113365 | A1 | * | 6/2003 | Schaberg et al. | 424/449 |
| 2006/0110433 | A1 | * | 5/2006 | Terahara et al. | 424/448 |
| 2007/0098766 | A1 | * | 5/2007 | Kawamura et al. | 424/443 |
| 2007/0196455 | A1 | * | 8/2007 | Kamiyama et al. | 424/448 |
| 2008/0131488 | A1 | * | 6/2008 | Kawamura et al. | 424/443 |
| 2010/0076112 | A1 | * | 3/2010 | Kamiyama et al. | 523/111 |

FOREIGN PATENT DOCUMENTS

| | | | | |
|---|---|---|---|---|
| EP | 1043020 | A1 * | 10/2000 | ........... A61K 31/155 |
| JP | 61251619 | A | 11/1986 | |
| JP | H04503357 | A | 6/1992 | |
| JP | 06040947 | A | 2/1994 | |
| JP | 2005-325101 | A | 11/2005 | |
| JP | 2006-348219 | A | 12/2006 | |
| JP | 2007137876 | A | 6/2007 | |
| JP | 2007-284378 | A | 11/2007 | |
| JP | 2008-208084 | A | 9/2008 | |
| JP | 2010241784 | A | 10/2010 | |
| WO | WO 00/44846 | * | 8/2000 | ............. C09J 133/04 |
| WO | 02/09653 | A1 | 2/2002 | |
| WO | WO 2004/026313 | A1 * | 4/2004 | ......... A61K 31/5415 |
| WO | WO2008133982 | A2 | 11/2008 | |

OTHER PUBLICATIONS

Morriston, R.T., et al., "Addition Reactions of Ammonia Derivatives", Organic Chemistry, 6th Ed., Mar. 1, 1995, pp. 866-867.
International Search Report issued for PCT/JP2010/064937, mailed Nov. 30, 2010.
Extended European Search Report issued for EP 10813735.7, mailed Apr. 23, 2013.
Kessel, Nicola et al., "The diacetone acrylamide crosslinking reaction and its influence on the film formation of an acrylic latex", J. Coat. Technol. Res., vol. 5(3), pp. 285-297, 2008.

(Continued)

*Primary Examiner* — Philip R Wiest
*Assistant Examiner* — Benjamin Klein
(74) *Attorney, Agent, or Firm* — Cantor Colburn LLP

(57) ABSTRACT

Disclosed is a transdermally absorbable preparation, in which an adhesive agent produced by crosslinking at least one copolymer is contained in an adhesive layer and the aging period in the production of the adhesive layer can be shortened. The transdermally absorbable preparation comprises a support and an adhesive layer arranged on the support and containing an adhesive agent and a medicinal component. The transdermally absorbable preparation is characterized in that the adhesive agent comprises a resin mixture comprising 100 parts by mass of a specific acrylic copolymer (A) and 0.1 to 30 parts by mass of a specific acrylic copolymer (B) or 0.05 to 2 part(s) by mass of a polyamine compound, and the adhesive layer additionally contains an organic acid.

13 Claims, No Drawings

(56) References Cited

OTHER PUBLICATIONS

Morrison, Robert T. and Boyd, Robert N., "Lehrbuch der Organischen Chemie", 2., berichtigte Auflage, Verlag Chemie, Weinheim, 1978, pp. 698-702.

Office Action issued to RU Application No. 2012113139, mailed Jul. 23, 2014.

Japanese Notice of Reasons for Rejection corresponding to Patent Application No. 2011-529919; Date of Mailing: Feb. 10, 2015.

* cited by examiner

TRANSDERMALLY ABSORBABLE PREPARATION

CROSS-REFERENCE TO RELATED APPLICATIONS

This application is the National Stage of International Application No. PCT/JP2010/064937, filed Sep. 1, 2010, which claims the benefit of Japanese Application No. 2009-206183, filed Sep. 7, 2009, the entire contents of both of which are incorporated by reference herein.

FIELD OF THE INVENTION

The present invention relates to a transdermally absorbable preparation, and more specifically relates to a transdermally absorbable preparation which has on one surface of a backing an adhesive layer containing at least an adhesive agent, and which is used by applying to the skin.

BACKGROUND OF THE INVENTION

Various types of transdermally absorbable preparations that administer a drug through the skin surface into a living body have been proposed that have a tape or sheet shape in which an adhesive layer containing a medicinal component is formed on one surface of a nonwoven fabric or plastic film. Thus, the type of transdermally absorbable preparation which is applied to the skin requires properties of maintaining a given level of blood concentration over a long time by containing a sufficient amount of a medicinal component in an adhesive layer.

From such standpoint, various types of cross-linking adhesive agent have been studied as an adhesive agent for a transdermally absorbable preparation. Patent Document 1, for example, proposes a type of cross-linking adhesive agent for the skin in which a copolymer A which comprises a (meth)acrylic acid alkyl ester as a main constituent and is copolymerized with diacetone acrylamide, and a copolymer B which comprises a (meth)acrylic acid alkyl ester as a main constituent and comprises a primary amino group and/or a carboxyhydrazide group on side chains are mixed and cross-linked.

Patent Document 1: Japanese Patent Application Laid-Open No. 2005-325101

SUMMARY OF THE INVENTION

Problems to be Solved by the Invention

The type of cross-linking adhesive agent as described in Patent Document 1 is preferably used as an adhesive agent for a transdermally absorbable preparation since a medicinal component and the like can be retained in a network structure formed throughout the entire adhesive agent by cross-linking.

In the meantime, the adhesive agent described in Patent Document 1 acquires the above network structure, as well as cohesion (hardness) required as an adhesive agent for a transdermally absorbable preparation since, by mixing the copolymer A and the copolymer B, they are cross-linked with each other to increase cross-linking degree. Since the cross-linking reaction proceeds with time, the cross-linking degree of an adhesive agent is not adequate and quality thereof is not stable for a while after mixing the copolymer A and the copolymer B. Thus, the step of leaving a transdermally absorbable preparation to be produced at, for example, room temperature, i.e. aging (maturation), is required until the cross-linking degree of the adhesive agent becomes adequate and the quality as a transdermally absorbable preparation becomes stable. The aging, however, requires for several days and is one of the factors that decreases the production rate (throughput) when a transdermally absorbable preparation using an adhesive agent as described above is produced. Such tendency is strengthened when a basic drug is used as a medicinal component. Thus, in particular, there has been a problem of a decrease in the production rate when a transdermally absorbable preparation containing a basic drug is produced.

The present invention was made in view of the above situations, and an object thereof is to provide a transdermally absorbable preparation, in which an adhesive agent produced by cross-linking one or more copolymers is contained in an adhesive layer and in which the aging period in producing the adhesive layer can be shortened.

Means for Solving the Problems

As a result of intensive study to solve the above problems, the present inventors found that the aging period can be shortened, even when using a basic drug as a medicinal component, by, unexpectedly, coexisting an organic acid when an acrylic copolymer (A) which comprises a (meth)acrylic acid alkyl ester as a main monomer component and which is copolymerized with diacetone acrylamide, and an acrylic copolymer (B) which comprises a (meth)acrylic acid alkyl ester as a main monomer component and which comprises a primary amino group and/or a carboxyhydrazide group on side chains are mixed and they are cross-linked to each other. The present inventors also found that the aging period when using a basic drug as a medicinal component can be shortened by coexisting an organic acid when the above acrylic copolymer (A) is cross-linked with a polyamine compound such as adipic acid dihydrazide. The present invention is completed based on the knowledge.

That is, the present invention is (1) a transdermally absorbable preparation having a backing and an adhesive layer which is placed on the backing and which contains an adhesive agent and a medicinal component, the transdermally absorbable preparation being characterized in that the adhesive agent comprises a resin mixture comprising 100 parts by mass of an acrylic copolymer (A) described below and 0.1 to 30 parts by mass of an acrylic copolymer (B) described below or 0.05 to 2 parts by mass of a polyamine compound and that the adhesive layer further comprises an organic acid.

Acrylic copolymer (A); an acrylic copolymer which comprises a (meth)acrylic acid alkyl ester as a main monomer component, and comprises 3 to 45% by mass of diacetone acrylamide as a prerequisite monomer component, but does not comprise a free carboxyl group.

Acrylic copolymer (B); an acrylic copolymer which comprises a (meth)acrylic acid alkyl ester as a main monomer component, and comprises a primary amino group and/or a carboxyhydrazide group on side chains, but does not comprise a free carboxyl group.

The present invention is (2) the transdermally absorbable preparation described in (1), comprising as the organic acid at least any of lactic acid, salicylic acid, succinic acid, thioglycolic acid, maleic acid, malonic acid, adipic acid, benzoic acid, capric acid, sorbic acid, malic acid, citric acid, tartaric acid, palmitic acid, fumaric acid, propionic acid, behenic acid, myristic acid and hydrates thereof.

The present invention is also (3) the transdermally absorbable preparation described in (1) or (2), wherein the medicinal component is nicotine or lidocaine, or salts thereof.

The present invention is (4) the transdermally absorbable preparation described in (3), wherein the medicinal component is nicotine or a salt thereof.

The present invention is (5) the transdermally absorbable preparation described in any one of (1) to (4), wherein the adhesive layer further comprises an antioxidant.

The present invention is (6) the transdermally absorbable preparation described in (5), wherein the antioxidant is dibutylhydroxytoluene.

The present invention is (7) the transdermally absorbable preparation described in any one of (1) to (6), further comprising a patching layer which provide a patching property for the skin, or sequentially comprising a controlled-release membrane which controls release of the medicinal component from the adhesive layer and a patching layer which provides the patching property for the skin on a surface of the adhesive layer.

Effects of the Invention

By the present invention, provided is a transdermally absorbable preparation, in which an adhesive agent produced by cross-linking one or more copolymers is contained in an adhesive layer, and in which the aging period in producing the adhesive layer can be shortened.

DETAILED DESCRIPTION OF THE INVENTION

The first embodiment of the transdermally absorbable preparation of the present invention The first embodiment of the transdermally absorbable preparation of the present invention will be now described.

The transdermally absorbable preparation of the present embodiment has a medicated surface on a backing, and is designed so that the active ingredient will be absorbed through the skin into a body, when the transdermally absorbable preparation is applied to bring the medicated surface into contact with the skin. Such preparations may include those designed to deliver an active ingredient into the systemic blood circulation through the skin, and those designed to topically deliver an active ingredient through the skin. The former is classified into "transdermal systems" in Japanese Pharmacopoeia, whereas the latter is classified into "patches" in Japanese Pharmacopoeia, and the transdermally absorbable preparation of the present invention may be of any of these types.

The transdermally absorbable preparation of the present embodiment has on one surface of a backing at least an adhesive layer. To the adhesive layer, a medicinal component is added, and the surface to be in contact with the skin of the adhesive layer corresponds to the medicated surface. The adhesive layer, the medicinal component and the backing will now be explained.

Adhesive Layer

The adhesive layer is a layer for providing a patching property of bonding a transdermally absorbable preparation to the skin. The adhesive layer contains a medicinal component, and the medicinal component is absorbed into the skin from the adhesive layer through the medicated surface. The adhesive layer contains an adhesive agent, a medicinal component, an organic acid and, as needed, other components. Among these, the medicinal component is described below, and the adhesive agent, the organic acid and other components will be explained here.

[Adhesive Agent]

The adhesive agent in the present embodiment comprises a resin mixture comprising 100 parts by mass of an acrylic copolymer (A) and 0.1 to 30 parts by mass of an acrylic copolymer (B), which are described below. In the resin mixture, a network structure can be formed by cross-linking the acrylic copolymer (A) and acrylic copolymer (B). Thus, the network structure is formed throughout the entire adhesive layer, and the transdermally absorbable preparation of the present embodiment can contain sufficient amounts of a medicinal component and the like by retaining the medicinal component and the like in the network structure. Therefore, the transdermally absorbable preparation of the present embodiment can maintain a blood concentration of an active ingredient at a given level for a long period of time.

The above acrylic copolymer (A) and acrylic copolymer (B) are acrylic resin which does not substantially comprise a free carboxyl group. Thus, in the transdermally absorbable preparation of the present embodiment, even when a medicinal component contained in the adhesive layer has properties of reacting with and bonding to a carboxyl group, a decline in transdermal absorbency which accompanies the reaction and bonding of the medicinal component with adhesive agent ingredients (acrylic copolymers) can be prevented. The phrase "not substantially comprise a free carboxyl group" means that all carboxyl groups are converted into substituents such as an ester bond in design terms. Of these, for example, a case where only a few ester bonds and the like are converted into free carboxyl groups by hydrolysis and a case where free carboxyl groups are contained as impurities derived from primary materials may be also contained.

The acrylic copolymer (A) contained in the above resin mixture is an acrylic copolymer which comprises a (meth) acrylic acid alkyl ester as a main monomer component, and 3 to 45% by mass of diacetone acrylamide as a prerequisite monomer component. The acryl copolymer (B) contained in the above resin mixture is also an acrylic copolymer which comprises a (meth)acrylic acid alkyl ester as a main monomer component, and a primary amino group and/or a carboxyhydrazide group on side chains. In such resin mixture, a fine network structure based on the cross-linking reaction of a carbonyl group derived from diacetone acrylamide contained in an acrylic copolymer (A) and a primary amino group and a carboxyhydrazide group contained in an acrylic copolymer (B) can be formed throughout the entire adhesive layer, and a medicinal component and the like can be retained in such network structure. Thus, the resin mixture can be preferably used for the adhesive layer of the transdermally absorbable preparation.

An example of production of an acrylic copolymer (A) includes a method in which to a (meth)acrylic acid alkyl ester, a main monomer component, diacetone acrylamide, also a monomer component, is added to be 3 to 45% by mass per the total monomers and the obtained mixture is radically polymerized. These monomer components can be polymerized according to a conventional method using a polymerization initiator such as a peroxidized compound or an azo compound. When these monomers are polymerized, it is preferred that a solvent be appropriately added to adjust the viscosity of the reaction solution.

As (meth)acrylic acid alkyl esters, a (meth)acrylic acid alkyl ester in which alkyl group thereof has 1 to 12 carbon atoms is preferably used. Specific examples include methyl (meth)acrylate, ethyl (meth)acrylate, propyl (meth)acrylate, butyl (meth)acrylate, 2-ethylhexyl (meth)acrylate, octyl (meth)acrylate, dodecyl (meth)acrylate and the like. These (meth)acrylic acid alkyl esters may be used individually or two or more of the esters may be used in combination.

In an acrylic copolymer (A), a number average molecular weight thereof is preferably 100,000 to 1,500,000 and a weight average molecular weight thereof is preferably 300,000 to 2,500,000. A molecular weight of an acrylic copolymer (A) within the above range is preferred because an adhesive layer of a transdermally absorbable preparation shows suitable adhesion to the skin. In the above range, the number average molecular weight of an acrylic copolymer (A) is more preferably 300,000 to 1,000,000 and most preferably 500,000 to 800,000. In the above range, the weight average molecular weight of an acrylic copolymer (A) is more preferably 500,000 to 2,000,000 and most preferably 1,000,000 to 1,500,000.

An example of production of an acrylic copolymer (B) includes a method in which to a (meth)acrylic acid alkyl ester, a main monomer component, a monomer component to introduce a primary amino group and/or a monomer component to introduce a carboxyhydrazide group are added to be 1 to 30% by mass per the total monomers and the obtained mixture is radically polymerized, and then side chains derived from the monomer components to introduce a carboxyhydrazide group are converted into carboxyhydrazide groups. The radical polymerization of the monomer components can be carried out according to a conventional method using a polymerization initiator such as a peroxidized compound or an azo compound. When the monomer components are radically polymerized, it is preferred that a solvent be appropriately added to adjust the viscosity of the reaction solution. As a (meth)acrylic acid alkyl ester used in producing an acrylic copolymer (B), the same as exemplified in the above acrylic copolymer (A) can be used.

Also, the number of primary amino group and/or carboxyhydrazide group in an acrylic copolymer (B) is preferably two or more, and more preferably three or more in a molecular chain of the acrylic copolymer (B) for showing suitable crosslinkability with an acrylic copolymer (A).

Moreover, it is preferred that a monomer component to introduce a primary amino group and/or a monomer component to introduce a carboxyhydrazide group, and a (meth)acrylic acid alkyl ester monomer be mixed to have the molar ratio of 1:5 to 1:100 and be copolymerized.

A monomer component to introduce a primary amino group into an acrylic copolymer (B) includes a compound having a vinyl group capable of polymerizing with a (meth)acrylic acid alkyl ester, and a primary amino group. Examples of such compound include vinylamine and the like.

A monomer component to introduce a carboxyhydrazide group into an acrylic copolymer (B) includes a compound having a vinyl group capable of polymerizing with a (meth)acrylic acid alkyl ester and a keto group capable of reacting with a hydrazide compound. Examples of such compound include diacetone acrylamide, acrolein, acetoacetoxyethyl methacrylate and the like.

To convert a side chain derived from a monomer component to introduce a carboxyhydrazide group into the carboxyhydrazide group, the polymer obtained by the above radical polymerization is dissolved in a polar solvent, and the obtained solution may be reacted with a dihydrazide of a dicarboxylic acid in the presence of an acid catalyst. Examples of the dihydrazides of dicarboxylic acids include adipic acid dihydrazide, glutaric acid dihydrazide, pimelic acid dihydrazide and the like.

In an acrylic copolymer (B), a number average molecular weight thereof is preferably 1,500 to 50,000 and a weight average molecular weight thereof is preferably 2,000 to 100,000. A molecular weight of an acrylic copolymer (B) which is not less than the above lower limit is preferred because gelation of a mixed liquid is inhibited and a coating property becomes good in producing an adhesive layer. A molecular weight of an acrylic copolymer (B) which is not more than the above upper limit is preferred because a suitable cross-linking state with an acrylic copolymer (A) can be obtained. In the above range, the number average molecular weight of an acrylic copolymer (B) is more preferably 2,000 to 10,000 and most preferably 3,000 to 8,000. In the above range, the weight average molecular weight of an acrylic copolymer (B) is more preferably 5,000 to 20,000 and most preferably 8,000 to 15,000.

The adhesive layer of the transdermally absorbable preparation of the present embodiment can contain an adhesive agent other than the above resin mixture for the purpose, for example, of improving a patching property to the skin and the like.

[Organic Acid]

An organic acid will be now described. An organic acid used in the present embodiment is contained in the adhesive layer, and has an action to promote cross-linking of an acrylic copolymer (A) and an acrylic copolymer (B). As described above, when two or more kinds of resin are mixed and cross-linked to form an adhesive layer just as the transdermally absorbable preparation of the present embodiment, such adhesive layer requires a aging period until the adhesive layer acquires necessary cohesion (hardness) by progression of cross-linking. The present inventors have regarded a long aging period, particularly when using a basic drug as a medicinal component, as a problem, and have explored a method capable of shortening the aging period. Consequently the present inventors found that, even when using a basic drug as a medicinal component, by, unexpectedly, further adding an organic acid to a mixture of an acrylic copolymer (A) and an acrylic copolymer (B), the cross-linking reaction of the acrylic copolymer (A) and the acrylic copolymer (B) is promoted and the aging period can be considerably shortened. The present invention is completed based on the knowledge.

An organic acid is added to a mixture of an acrylic copolymer (A) and an acrylic copolymer (B). An example method of adding an organic acid includes a method in which the acrylic copolymer (A) and the acrylic copolymer (B) are dissolved in a solvent to produce a mixed solution, and an organic acid, a medicinal component and the like described below are further dissolved in the mixed solution, followed by applying the obtained solution to a backing, and then the solvent contained in the mixed solution applied is evaporated to form the adhesive layer. In this case, the amount of the mixed solution to be applied to the backing can be appropriately determined to obtain a desired thickness of the adhesive layer after evaporating the solvent. After the solvent is evaporated to form the adhesive layer, the cross-linking reaction of the acrylic copolymer (A) and the acrylic copolymer (B) contained in the adhesive layer is initiated, and aging may be carried out until the adhesive layer acquires sufficient cohesion by progression of the cross-linking reaction. As used herein, cohesion represents hardness of the adhesive layer. Low cohesion may lead to problems that a transdermally absorbable preparation is spontaneously released when it is applied to the skin, and the adhesive layer remains on the skin when the transdermally absorbable preparation is released.

Examples of the organic acid used for the transdermally absorbable preparation of the present embodiment include lactic acid, salicylic acid, succinic acid, thioglycolic acid, maleic acid, malonic acid, adipic acid, benzoic acid, capric acid, sorbic acid, malic acid, citric acid, tartaric acid, palmitic acid, fumaric acid, propionic acid, behenic acid, myristic acid and hydrates thereof, and the like. Among these, lactic acid is most preferably used. Although inorganic acids such as hydrochloric acid, phosphoric acid and the like other than organic acids are present as an acid, an organic acid is used in the present invention because an inorganic acid has an exceedingly limited effect to promote the cross-linking reaction of an acrylic copolymer (A) and an acrylic copolymer (B).

The amount of an organic acid to be used is preferably 0.05 to 5% by mass, more preferably 0.1 to 2% by mass and most preferably 0.3 to 1% by mass per the total mass of an adhesive layer. When the amount of an organic acid to be used is 0.05% by mass or more per the total mass of an adhesive layer, the cross-linking reaction of an acrylic copolymer (A) and an acrylic copolymer (B) can be successfully promoted. In addition, when the amount of an organic acid to be used is 5% by mass or less per the total mass of an adhesive layer, skin irritation caused by applying a transdermally absorbable preparation to the skin can be relieved.

[Other Components]

The other components contained in an adhesive layer, as needed, will be now described. These components are a variety of additives which are added to an adhesive layer, as needed, to provide a variety of functions for a transdermally absorbable preparation. Examples of such additives include plasticizers, antioxidants, solvents for dissolving a medicinal component, a variety of adhesive agents, antiseptic agents, pH adjusting agents, chelating agents, transdermal absorption promoters, excipients, flavors, coloring materials and the like.

As a plasticizer, an oily material having a high boiling point may be generally used. Examples of the plasticizer include fatty acid ester derivatives such as isopropyl myristate, diethyl sebacate, diisopropyl adipate, ethyl oleate, isopropyl palmitate, ethyl laurate, octyl palmitate, isotridecyl myristate and medium chain fatty acid triglyceride; higher alcohol derivatives such as hexyl decanol and octyl dodecanol; polyalkylene glycols such as polyethylene glycol and polypropylene glycol; fats and oils such as olive oil and castor oil, and the like. Among these, isopropyl myristate, isopropyl palmitate and the like are preferred due to not only acting as a plasticizer of an adhesive agent but also having effects of promoting diffusion of a medicinal component in a transdermally absorbable preparation and promoting skin penetration of a medicinal component. These can be used individually or two or more of them can be used in combination. The amount of a plasticizer to be added is preferably 1 to 40% by mass, more preferably 5 to 35% by mass, and most preferably 6 to 30% by mass per the total mass of an adhesive layer. When using a type of adhesive agent in which an acrylic copolymer (A) and an acrylic copolymer (B) are mixed and cross-linked just as the present embodiment, in particular if an oily matter such as nicotine is used as a medicinal component, a good transdermally absorbable preparation can be obtained without using a plasticizer. In this case, a plasticizer may not necessarily used.

An antioxidant inhibits oxidation of components contained in an adhesive layer, and a coloration phenomenon of the adhesive layer (a medicated surface) observed when storing a transdermally absorbable preparation for a long period of time is reduced. Thus, the preservation stability of a transdermally absorbable preparation can be improved. Examples of such antioxidant include phenol antioxidants such as dibutylhydroxytoluene (BHT, IUPAC name: 2,6-bis(1,1-dimethylethyl)-4-methylphenol) and dibutylated hydroxyanisole (BHA); ascorbic acid, tocopherol, tocopherol ester derivatives, 2-mercaptobenzimidazole and the like. Among these antioxidants, preferred is dibutylhydroxytoluene (BHT). The amount of an antioxidant to be used is preferably 0.1 to 20% by mass and more preferably 0.5 to 10% by mass per the total mass of an adhesive layer.

A solvent for dissolving a medicinal component is not particularly limited as long as it dissolves a drug, and is preferably a solvent which does not cause skin irritation. Examples of such solvent include lower alcohols such as ethanol, propanol and isopropanol; medium alcohols such as hexanol and octanol; polyalcohols such as glycerin, ethylene glycol and diethylene glycol; fatty acid esters, polyvinyl alcohols, N-methylpyrrolidone, lactic acid, and the like. These can be used individually or two or more of them can be used in combination.

As simply described above, an example of forming an adhesive layer in the transdermally absorbable preparation of the present embodiment includes a method in which components to be contained in the adhesive layer such as the above resin mixture, an organic acid, a medicinal component and the like are dissolved in a solvent to produce a solution, and the solvent contained in the solution is heated and evaporated by a known method. The solvent to be used in such method is not particularly limited as long as it is an organic solvent which is evaporated during the step of drying by heating in production of a transdermally absorbable preparation. Examples thereof can include organic solvents, e.g., ketones such as acetone and methyl ethyl ketone; acetic acid esters such as methyl acetate, ethyl acetate, propyl acetate and butyl acetate; aliphatic hydrocarbons such as hexane, heptane, octane and cyclohexane; aromatic hydrocarbons such as benzene, toluene and xylene; ethers such as isopropyl ether, tetrahydrofuran and dioxane; and the like. These can be used individually or two or more of them can be used in combination.

Medicinal Component

A medicinal component used in the transdermally absorbable preparation of the present embodiment is contained in the adhesive layer, and is absorbed into the skin through a medicated surface corresponding to a surface of the adhesive layer and a contact surface with the skin. A kind of medicinal component used in the transdermally absorbable preparation of the present embodiment is not particularly limited. As described herein, when using a basic drug as a medicinal component, the progression of the cross-linking reaction of an acrylic copolymer (A) and an acrylic copolymer (B), which are adhesive agents, is delayed. Thus, there is a tendency to prolong the aging period in producing a transdermally absorbable preparation. From this standpoint, the effect of promoting the cross-linking reaction by adding the above organic acid will be further produced when using a basic drug as a medicinal component.

Examples of the medicinal component include smoking-cessation aids such as nicotine; regional anesthetics such as lidocaine hydrochloride, procaine hydrochloride and lidocaine; narcotic analgesics such as morphine sulfate, fentanyl citrate and fentanyl; antidementia drugs such as donepezil hydrochloride; dysuria improving drugs such as tamsulosin hydrochloride; sedative-hypnotic drugs such as flurazepam hydrochloride and rilmazafone hydrochloride; anti-inflammatory analgesic agents such as butorphanol tartrate and perisoxal citrate; psychostimulants such as methamphetamine hydrochloride and methylphenidate hydrochloride; psychoneurotic agents such as chlorpromazine hydrochloride, imipramine hydrochloride, risperidone, aripiprazole and olanzapine; skeletal muscle relaxants such as tizanidine hydrochloride, eperisone hydrochloride and pridinol mesylate; autonomic agents such as carpronium chloride and neostigmine bromide; anti parkinson agents such as trihexyphenidyl hydrochloride, amantadine hydrochloride and pergolide mesylate; antihistamines such as clemastine fumarate and diphenhydramine tannate; bronchodilators such as tulobuterol hydrochloride and procaterol hydrochloride; cardiotonic drugs such as isoprenaline hydrochloride and dopamine hydrochloride; coronary vasodilators such as diltiazem hydrochloride and verapamil hydrochloride; peripheral vasodilators such as nicametate citrate and tolazoline hydrochloride; cardiovascular preparations such as flunarizine hydrochloride and nicardipine hydrochloride; antiarrhythmic agents such as propranolol hydrochloride and alprenolol hydrochloride; anti-allergic agents such as ketotifen fumarate and azelastine hydrochloride; antimotion sickness agents such as betahistine mesylate and difenidol hydrochloride; antiemetic serotonin receptor antagonists; and the like. Among these, in particular, nicotine, lidocaine and fentanyl are preferably used.

The above medicinal components can be used in a free base form and in a pharmaceutically acceptable acid addition salt form, and the both forms can be used in combination. Although in an acid addition salt of a basic drug, aqueous solution thereof may show neutral to acid due to an acid to be added, such acid addition salt is also called a basic drug in the present invention. The amount of the above medicinal component to be used is preferably 1 to 60% by mass per the total mass of an adhesive layer in terms of preparation physicality and transdermal drug absorbability. The above medicinal components can be used individually or two or more of them can be used in combination.

Backing

Preferably a backing is impermeable or poorly permeable to a medicinal component, and is flexible. Specific examples include films of resin such as polyethylene, polypropylene, an ethylene-vinyl acetate copolymer, an ethylene-vinyl acetate-carbon monoxide copolymer, an ethylene-butyl acrylate-carbon monoxide copolymer, nylon, polyester (polyethylene terephthalate), polybutylene terephthalate and the like, as well as aluminum sheets, and the like. These may be laminated and processed into a sheet, or may be laminated together with woven fabric or nonwoven fabric. Furthermore, in order to improve the adhesion with an adhesive layer, a surface of a backing may be subjected to surface treatment such as corona treatment, plasma discharge treatment and the like, and subjected to anchor coating treatment with an anchor agent. The second embodiment of the transdermally absorbable preparation of the present invention The second embodiment of the transdermally absorbable preparation of the present invention will be now described. In the following description of the second embodiment, overlapping contents with those of the above first embodiment are abbreviated and different parts will be mainly described.

The transdermally absorbable preparation of the present embodiment differs from the above first embodiment in using as an adhesive agent a resin mixture comprising 100 parts by mass of the above acrylic copolymer (A) and 0.05 to 2 parts by mass of a polyamine compound, and the rest is the same as the above first embodiment. Thus, the polyamine compound will be described in the following description.

[Polyamine Compound]

The polyamine compound used in the present embodiment is a low molecular compound. As used herein, a low molecular compound means a monomolecular compound not forming a polymer or an oligomer by polymerization. A polyamine compound is a compound having two or more amino groups in a molecule. As described above, an acrylic copolymer (A) is a copolymer produced by polymerizing diacetone acrylamide as a prerequisite monomer, and comprises a keto group derived from diacetone acrylamide in the molecule. A polyamine compound is cross-linked with an acrylic copolymer (A) by reacting the keto group and an amino group contained in the polyamine compound.

Example of the polyamine compound most simply include hydrazine or a hydrazine hydrate compound. In view of being capable of showing good reactivity to the keto group derived from diacetone acrylamide contained in an acrylic copolymer (A), however, the amino groups contained in a polyamine compound are preferably bonded to other nitrogen atoms. Examples of such compounds include polyhydrazide compounds obtained by acting a hydrazine compound to a polybasic organic acid.

Preferred examples of the polyhydrazide compound include dihydrazides of dicarboxylic acids. Examples of such compounds include phthalic acid dihydrazide, isophthalic acid dihydrazide, terephthalic acid dihydrazide, oxalic acid dihydrazide, sebacic acid dihydrazide, adipic acid dihydrazide and the like. Particularly preferred polyhydrazide compounds include saturated aliphatic dicarboxylic acids, among these, dihydrazides of saturated aliphatic dicarboxylic acids having 2 to 10 carbon atoms. Examples of such compounds include oxalic acid dihydrazide, sebacic acid dihydrazide and adipic acid dihydrazide. Among these, preferred is adipic acid dihydrazide. Adipic acid dihydrazide is also called adipic acid diamine or adipohydrazide.

The above polyamine compound is mixed with an acrylic copolymer (A) to be a resin mixture, which is an adhesive agent. The amount of a polyamine compound to be added is 0.05 to 2 parts by mass and more preferably 0.1 to 1 part by mass per 100 parts by mass of an acrylic copolymer (A). When the amount of a polyamine compound to be added is 0.05 parts by mass or more per 100 parts by mass of an acrylic copolymer (A), the acrylic copolymer (A) can be successfully cross-linked and an adhesive agent having appropriate cohesion can be obtained. When the amount of a polyamine compound to be added is 2 parts by mass or less per 100 parts by mass of an acrylic copolymer (A), gelation of the acrylic copolymer (A) can be inhibited.

The above resin mixture, as well as a medicinal component, an organic acid and, as needed, other components are dissolved in a solvent to prepare a solution, and the solution is applied to a surface of a base to form an adhesive layer on the surface of the base. The procedure is the same as in the description of the first embodiment, and is abbreviated here.

In the present embodiment, as the first embodiment described above, the adhesive layer also contains an organic acid. As well as the cross-linking reaction of an acrylic copolymer (A) and an acrylic copolymer (B) as described above, although the cross-linking reaction of an acrylic copolymer (A) with a polyamine compound in the present embodiment may be delayed when using a basic drug as a medicinal component, the delay is inhibited due to containing an organic acid in the adhesive layer. Thus, even when using a basic drug as a medicinal component, the aging period after producing a transdermally absorbable preparation can be shortened and the production rate in producing a transdermally absorbable preparation can be improved.

The Third Embodiment of the Transdermally Absorbable Preparation of the Present Invention The third embodiment of the transdermally absorbable preparation of the present invention will be now described. In the following description of the third embodiment, overlapping contents with those of the above first embodiment and second embodiment are abbreviated and different parts will be mainly described.

The transdermally absorbable preparation of the present embodiment has an "adhesive layer" described in the first and the second embodiments as a drug retaining layer. The transdermally absorbable preparation of the present embodiment has as a contact surface with the skin a "patching layer" to attach the transdermally absorbable preparation on the skin and to absorb a medicinal component contained in the transdermally absorbable preparation into the skin. A controlled-release membrane is set up, as needed, between the above drug retaining layer and patching layer. That is, the transdermally absorbable preparation of the present embodiment includes, from the opposite side of the skin to which the transdermally absorbable preparation is applied, a backing, a drug retaining layer, a controlled-release membrane and a patching layer which are sequentially formed, or a backing, a drug retaining layer and a patching layer which are sequentially formed. The drug retaining layer is identical with the "adhesive layer" as described above, and can successfully retain a medicinal component in the inside of a network structure formed by cross-linking. The transdermally absorbable preparation of such embodiment is also included within the scope of the invention because of having a given adhesive layer (a drug retaining layer) on one surface of a backing.

The transdermally absorbable preparations of the above first and second embodiments have as a contact surface with the skin an "adhesive layer" having a good patching property to the skin and a drug retaining property. Thus, although the transdermally absorbable preparations of the first and the second embodiments have a good drug delivery action to the skin, the good drug delivery action may be excessive depending on the kinds of medicinal component. Accordingly, in the transdermally absorbable preparation of the present embodiment, an "adhesive layer" containing a medicinal component is used as the drug retaining layer which does not contact the skin, and a controlled-release membrane to control the delivery rate of a medicinal component from the drug retaining layer is set up, as needed, between the drug retaining layer and a patching layer which is a contact surface with the skin. When a transdermally absorbable preparation does not have a controlled-release membrane, the above patching layer controls the delivery rate of a medicinal component from the drug retaining layer. The transdermally absorbable preparation of the present embodiment is preferably used for a medicinal component particularly needed to maintain a stable blood concentration for a long period of time.

The drug retaining layer of the present embodiment is identical with the "adhesive layer" described above, and is not described here. Since the "adhesive layer" (i.e. a drug retaining layer) in the present embodiment is not a layer to be directly applied to the skin, a patching property is not essential.

A controlled-release membrane is set up between a drug retaining layer and a patching layer, and controls a delivery rate of a medicinal component from the drug retaining layer to the patching layer. By this, the delivery rate of a medicinal component from the transdermally absorbable preparation to the skin is controlled.

Known controlled-release membranes can be used without particular restriction. An example of such controlled-release membrane includes ethylene-vinyl acetate copolymer (EVA) or a polyethylene porous membrane. A thickness, quality, a hole size to be formed and the like of the membrane can be appropriately determined in view of the desired delivery rate of a medicinal component. A method in which a layer of a controlled-release membrane is set up in the transdermally absorbable preparation is not particularly limited, and an example thereof includes a method in which a controlled-release membrane processed into a sheet is pressingly arranged on an adhesive surface of a drug retaining layer formed on a surface of a backing.

A patching layer is set to attach a transdermally absorbable preparation to the skin. The patching layer is a contact surface with the skin in a transdermally absorbable preparation, thus it has a role to deliver a medicinal component to the skin. Further, in the form of not using the above controlled-release membrane, such patching layer has a function to control the drug delivery rate from the drug retaining layer.

A material to form a patching layer is not particularly limited as long as it has adhesion, and examples thereof include rubber materials such as polyisobutylene, styrene-isoprene-styrene block copolymer and natural rubber; acrylic materials such as acrylates-octyl acrylate copolymer, 2-ethylhexyl acrylate-2-ethylhexyl methacrylate-dodecyl methacrylate copolymer and 2-ethylhexyl acrylate-diacetone acrylamide-acetoacetoxyethyl methacrylate-methyl methacrylate copolymer; and the like. These materials can be used individually or several materials can be used in combination. A method of forming a patching layer is not particularly limited, and examples thereof include a method in which the above material is dissolved in a suitable solvent and then the solution is applied to a surface of a controlled-release membrane, followed by drying it; a method in which the above material is processed into a sheet and the sheet is then pressingly arranged on a surface of a controlled-release membrane; and the like. A thickness of the patching layer is not particularly limited, and can be appropriately determined in view of properties needed for a transdermally absorbable preparation.

To the patching layer, a tackifier, a plasticizer, an antioxidant, a stabilizer and the like other than the above materials can be added, as needed.

The transdermally absorbable preparation of the present invention was described by way of specific embodiments. The present invention is not, however, limited to the above embodiments and may be practiced with modification and alteration within the scope of constitution of the present invention.

EXAMPLES

The transdermally absorbable preparation of the present invention will now be described in more detail by way of examples thereof. It should be noted, however, that the present invention is not limited to the following examples.

Production Example

Production of Adhesive Agent (Resin Mixture)

A solution of an acrylic copolymer (A) and a solution of an acrylic copolymer (B) obtained according to synthesis methods described below were mixed so that a mass ratio of resin contained in the solution would be 100:5 (acrylic copolymer (A): acrylic copolymer (B)) to produce an adhesive agent (a resin mixture).

Acrylic Copolymer (A)

To 200 parts by mass of 2-ethylhexyl acrylate, 100 parts by mass of butyl acrylate, 50 parts by mass of diacetone acrylamide and 300 parts by mass of ethyl acetate were added and mixed. This mixture was transferred into a separable flask equipped with a stirrer and a reflux condenser, and it was heated to 75° C. while stirring and performing nitrogen replacement. A solution in which 2 parts by mass of benzoyl peroxide was dissolved in 20 parts by mass of ethyl acetate was divided into five aliquots, and one aliquot was added to the separable flask to initiate a polymerization reaction. Each one aliquot of the remaining four aliquots was added at one hour intervals after 2 hours from initiation of the polymerization reaction. After completion of the addition, the reaction was carried out for another 2 hours. After initiation of the reaction, 50 parts by mass of ethyl acetate was added four times at 2 hour intervals to adjust viscosity. After completion of the reaction, the reaction mixture was cooled, and ethyl acetate was then added thereto to obtain a solution of the acrylic copolymer (A) with 30% by mass of solid concentration. In the obtained acrylic copolymer (A), the number average molecular weight was about 680,000 and the weight average molecular weight was about 1,200,000.

Acrylic Copolymer (B)

To 660 parts by mass of ethyl acrylate, 70 parts by mass of diacetone acrylamide, 40 parts by mass of dodecyl mercaptan as a molecular weight modifier and 400 parts by mass of ethyl acetate were added and mixed. This mixture was transferred into a separable flask equipped with a stirrer and a reflux condenser, and it was heated to 70° C. while stirring and performing nitrogen replacement. A solution in which 5 parts by mass of azobisisobutyronitrile was dissolved in 100 parts by mass of ethyl acetate was divided into five aliquots, and one aliquot was added to the separable flask to initiate a polymerization reaction. Each one aliquot of the remaining four aliquots was added at 1 hour intervals after 2 hours from initiation of the polymerization reaction. After completion of the addition, the reaction was carried out for another 2 hours. After initiation of the reaction, 50 parts by mass of ethyl acetate was added four times at 2 hour intervals to adjust viscosity. Thereafter, a solution in which 40 parts by mass of adipic acid dihydrazide was dissolved in a mixed liquid of 40 parts by mass of purified water, 1,600 parts by mass of methanol and 260 parts by mass of ethyl acetate was added thereto, and 5 parts by mass of concentrated hydrochloric acid was further added thereto, and the obtained mixture was then heated to 70° C. After completion of the reaction, the reaction mixture was cooled, and then washed with purified water three times. The obtained product was dissolved in a mixed solvent of 700 parts by mass of ethyl acetate, 1,400 parts by mass of acetone and 400 parts by mass of methanol to obtain a solution of the acrylic copolymer (B) with 30% by mass of solid concentration. In the obtained acrylic copolymer (B), the number average molecular weight was about 6,500 and the weight average molecular weight was about 11,000.

Examples 1 to 11

To the solution of an adhesive agent (a resin mixture) obtained in the above production example, nicotine (a free form) as a medicinal component and a variety of organic acids were added, and the entire solution was stirred uniformly to obtain a mixed liquid. In order to obtain an adhesive layer of 67 μm thick after drying, this mixed liquid was applied to a backing, the backing having a coating surface which was subjected to corona treatment and being a PET (polyethylene terephthalate) film of 25 μm thick, and was dried to form an adhesive layer. The transdermally absorbable preparations of Examples 1 to 11 were produced. The organic acids used in each example are shown in Table 1. Each component was added so that a value of % by mass after drying would be as shown in Table 1. Each value shown in Table 1 means % by mass.

Comparative Examples 1 to 3

The transdermally absorbable preparations of Comparative Examples 1 to 3 were produced by the same procedures as in the above Examples 1 to 11 except that an inorganic acid was added in place of an organic acid or no acid was added. Each component was added so that a value of % by mass after drying would be as shown in Table 2. Each value shown in Table 2 means % by mass.

[Evaluation of Cross-Linking Rate]

Each transdermally absorbable preparation of Examples 1 to 11 and Comparative Examples 1 to 3 was left at 25° C. after being produced, and time (days) for which the adhesive layer took to acquire cohesion not retaining an adhesive agent on the skin was examined. The time corresponds to the aging period. The shorter time indicates a faster cross-linking rate of the adhesive agent. The results are shown in Tables 1 and 2.

TABLE 1

|  | Example | | | | | | | | | | |
| --- | --- | --- | --- | --- | --- | --- | --- | --- | --- | --- | --- |
|  | 1 | 2 | 3 | 4 | 5 | 6 | 7 | 8 | 9 | 10 | 11 |
| adhesive agent | 52.6 | 52.6 | 52.6 | 52.6 | 52.6 | 52.6 | 52.6 | 52.6 | 52.6 | 52.6 | 52.6 |
| nicotine | 46.7 | 46.7 | 46.7 | 46.7 | 46.7 | 46.7 | 46.7 | 46.7 | 46.7 | 46.7 | 46.7 |
| lactic acid | 0.7 | — | — | — | — | — | — | — | — | — | — |
| salicylic acid | — | 0.7 | — | — | — | — | — | — | — | — | — |
| succinic acid | — | — | 0.7 | — | — | — | — | — | — | — | — |
| thioglycolic acid | — | — | — | 0.7 | — | — | — | — | — | — | — |
| maleic acid | — | — | — | — | 0.7 | — | — | — | — | — | — |
| malonic acid | — | — | — | — | — | 0.7 | — | — | — | — | — |
| adipic acid | — | — | — | — | — | — | 0.7 | — | — | — | — |
| benzoic acid | — | — | — | — | — | — | — | 0.7 | — | — | — |
| capric acid | — | — | — | — | — | — | — | — | 0.7 | — | — |
| sorbic acid | — | — | — | — | — | — | — | — | — | 0.7 | — |
| malic acid | — | — | — | — | — | — | — | — | — | — | 0.7 |
| aging period taken | 1 day | 1 day | 1 day | 1 day | 1 day | 1 day | 2 days | 1 day | 3 days | 2 days | 2 days |

TABLE 2

|  | Comparative Example | | |
|---|---|---|---|
|  | 1 | 2 | 3 |
| adhesive agent | 52.6 | 52.6 | 53.3 |
| nicotine | 46.7 | 46.7 | 46.7 |
| hydrochloric acid | 0.7 | — | — |
| phosphoric acid | — | 0.7 | — |
| aging period taken | 14 days | 11 days | 11 days |

Examples 12 to 33

The transdermally absorbable preparations of Examples 12 to 33 were produced by the same procedures as in the above Examples 1 to 11 except that lidocaine was used as a medicinal component and isopropyl myristate (IPM) was added as a plasticizer. The organic acids used in each Example are shown in Tables 3 and 4. Each component was added so that a value of % by mass after drying would be as shown in Tables 3 and 4. Each value shown in Tables 3 and 4 means % by mass.

The cross-linking rates of the transdermally absorbable preparations of Examples 12 to 33 were also evaluated by the same method as for the transdermally absorbable preparations of the above Examples 1 to 11 and Comparative Examples 1 to 3. The results are shown in Tables 3 and 4.

Comparative Examples 4 to 6

The transdermally absorbable preparations of Comparative Examples 4 to 6 were produced by the same procedures as in the above Examples 12 to 33 except that an inorganic acid was added in place of an organic acid. Each component was added so that a value of % by mass after drying would be as shown in Table 5. Each value shown in Table 5 means % by mass.

The cross-linking rates of the transdermally absorbable preparations of Comparative Examples 4 to 6 were also evaluated by the same method as for the transdermally absorbable preparations of the above Examples 1 to 11 and Comparative Examples 1 to 3. The results are shown in Table 5.

TABLE 3

|  | Example | | | | | | | | | | |
|---|---|---|---|---|---|---|---|---|---|---|---|
|  | 12 | 13 | 14 | 15 | 16 | 17 | 18 | 19 | 20 | 21 | 22 |
| adhesive agent | 51.95 | 51.9 | 51.7 | 51.5 | 51.0 | 51.5 | 51.5 | 51.5 | 51.5 | 51.5 | 51.5 |
| lidocaine | 18.0 | 18.0 | 18.0 | 18.0 | 18.0 | 18.0 | 18.0 | 18.0 | 18.0 | 18.0 | 18.0 |
| IPM | 30.0 | 30.0 | 30.0 | 30.0 | 30.0 | 30.0 | 30.0 | 30.0 | 30.0 | 30.0 | 30.0 |
| lactic acid | 0.05 | 0.1 | 0.3 | 0.5 | 1.0 | — | — | — | — | — | — |
| salicylic acid | — | — | — | — | — | 0.5 | — | — | — | — | — |
| adipic acid | — | — | — | — | — | — | 0.5 | — | — | — | — |
| capric acid | — | — | — | — | — | — | — | 0.5 | — | — | — |
| succinic acid | — | — | — | — | — | — | — | — | 0.5 | — | — |
| sorbic acid | — | — | — | — | — | — | — | — | — | 0.5 | — |
| thioglycolic acid | — | — | — | — | — | — | — | — | — | — | 0.5 |
| aging period taken | 3 days | 2 days | 1 day | 1 day | 1 day | 1 day | 3 days | 3 days | 1 day | 3 days | 1 day |

TABLE 4

|  | Example | | | | | | | | | | |
|---|---|---|---|---|---|---|---|---|---|---|---|
|  | 23 | 24 | 25 | 26 | 27 | 28 | 29 | 30 | 31 | 32 | 33 |
| adhesive | 51.5 | 51.5 | 51.5 | 51.5 | 51.5 | 51.5 | 51.5 | 51.5 | 51.5 | 51.5 | 51.5 |
| lidocaine | 18.0 | 18.0 | 18.0 | 18.0 | 18.0 | 18.0 | 18.0 | 18.0 | 18.0 | 18.0 | 18.0 |
| IPM | 30.0 | 30.0 | 30.0 | 30.0 | 30.0 | 30.0 | 30.0 | 30.0 | 30.0 | 30.0 | 30.0 |
| citric acid | 0.5 | — | — | — | — | — | — | — | — | — | — |
| tartaric acid | — | 0.5 | — | — | — | — | — | — | — | — | — |
| palmitic acid | — | — | 0.5 | — | — | — | — | — | — | — | — |
| fumaric acid | — | — | — | 0.5 | — | — | — | — | — | — | — |
| propionic acid | — | — | — | — | 0.5 | — | — | — | — | — | — |
| behenic acid | — | — | — | — | — | 0.5 | — | — | — | — | — |
| myristic acid | — | — | — | — | — | — | 0.5 | — | — | — | — |
| maleic acid | — | — | — | — | — | — | — | 0.5 | — | — | — |
| malonic acid | — | — | — | — | — | — | — | — | 0.5 | — | — |

TABLE 4-continued

|  | Example | | | | | | | | | | |
|---|---|---|---|---|---|---|---|---|---|---|---|
|  | 23 | 24 | 25 | 26 | 27 | 28 | 29 | 30 | 31 | 32 | 33 |
| malic acid | — | — | — | — | — | — | — | — | — | 0.5 | — |
| benzoic aid | — | — | — | — | — | — | — | — | — | — | 0.5 |
| aging period taken | 5 days | 5 days | 5 days | 5 days | 5 days | 5 days | 5 days | 1 day | 1 day | 1 day | 1 day |

TABLE 5

|  | Comparative Example | | |
|---|---|---|---|
|  | 4 | 5 | 6 |
| adhesive | 51.5 | 51.5 | 51.5 |
| lidocaine | 18.0 | 18.0 | 18.0 |
| IPM | 30.0 | 30.0 | 30.0 |
| hydrochloric acid | 0.5 | — | — |
| sulfuric acid | — | 0.5 | — |
| phosphoric acid | — | — | 0.5 |
| aging period taken | 14 days | 11 days | 11 days |

[Evaluation of Amount of Drug Permeation]

From the skin of Yucatan Micro Pig (aged 5 months, female), unnecessary fat under the skin and the like were removed, and the skin was punched out in a suitable, certain size. A transdermally absorbable preparation for test was applied to one surface of the skin, and cumulative amounts of drug permeation were examined by measuring cumulative amounts of nicotine eluted into a receiver through the skin each at 4 hours, 8 hours and 24 hours after the onset of the test. The results are shown in Table 6. The test was performed using the transdermally absorbable preparation of Example 1 and a commercially available nicotine patch (NICO-DERM™), and areas of the medicated surfaces of the transdermally absorbable preparations used in the test were 0.95 cm$^2$ for the transdermally absorbable preparation of Example 1 and 1.77 cm$^2$ for the commercially available nicotine patch.

TABLE 6

|  | nicotine amount eluting into receiver (μg) | | |
|---|---|---|---|
|  | at 4 hours | at 8 hours | at 24 hours |
| Example 1 | 151.4 ± 87.8 | 744.3 ± 307.2 | 1915.7 ± 257.4 |
| control | 164.2 ± 80.3 | 663.2 ± 206.4 | 1863.4 ± 240.11 |

Evaluation of Coloration Inhibiting Effect of Antioxidant

Examples 34 to 38

To the solution of the adhesive agent (a resin mixture) obtained in the above production example, nicotine (a free form) as a medicinal component, lactic acid as an organic acid and dibutylhydroxytoluene (BHT, IUPAC name: 2,6-bis(1,1-dimethylethyl)-4-methylphenol) as an antioxidant were added, and the entire solution was stirred uniformly to obtain a mixed liquid. In order to obtain the adhesive layer of 67 μm thick after drying, this mixed liquid was applied to a backing, the backing having a coating surface which was subjected to corona treatment and being a PET film of 25 μm thick, and was dried to form an adhesive layer. The transdermally absorbable preparations of Examples 34 to 38 were produced. Each component was added so that a value of % by mass after drying would be as shown in Table 7. Each value shown in Table 7 means % by mass.

The transdermally absorbable preparations of Examples 34 to 38 were left at 40° C. for a month, and degree of coloration of an adhesive layer (a medicated surface) from the production of the transdermally absorbable preparations was evaluated by color difference (ΔE). The results are shown in Table 7. For color difference (ΔE), chromaticity of a surface of the adhesive layer was measured using a spectrophotometer (Model SP64, manufactured by X-Rite Inc.), and changes in chromaticity of the preparations immediately after being produced and after being left at 40° C. for a month were obtained by calculating using the following formula. When the degree of white-black, red-green and blue-yellow is represented as L-scale, a-scale and b-scale respectively, the color difference is represented as the square root of sum of squares of each scale difference $\Delta E = ((\Delta a)^2 + (\Delta b)^2 + (\Delta L)^2)^{1/2}$.

TABLE 7

|  | Example | | | | |
|---|---|---|---|---|---|
|  | 34 | 35 | 36 | 37 | 38 |
| adhesive | 52.6 | 52.1 | 51.6 | 49.6 | 47.6 |
| nicotine | 46.7 | 46.7 | 46.7 | 46.7 | 46.7 |
| lactic acid | 0.7 | 0.7 | 0.7 | 0.7 | 0.7 |
| BHT | — | 0.5 | 1.0 | 3.0 | 5.0 |
| color difference (ΔE) | 10.5 | 2.4 | 2.1 | 1.3 | 1.0 |

As shown in Tables 1, 3 and 4, it is revealed that the transdermally absorbable preparations of Examples 1 to 33 comprising an organic acid in the adhesive layer took about 1 to 5 days after being produced to acquire sufficient cohesion of the adhesive layer (that is, degree of the cross-linking reaction of an acrylic copolymer (A) and an acrylic copolymer (B) became sufficient). On the contrary, as shown in Tables 2 and 5, it is revealed that the transdermally absorbable preparations of Comparative Examples 1 to 6 comprising an inorganic acid in the adhesive layer and not comprising an acid took 11 days or more to acquire sufficient cohesion of the adhesive layer. Thus, it is understood that the cross-linking reaction of an acrylic copolymer (A) and an acrylic copolymer (B) contained in the adhesive agent was promoted by adding an organic acid to an adhesive layer, and the aging period after producing a transdermally absorbable preparation could be shortened. It is understood that such tendency was observed both when using nicotine and when using lidocaine as a medicinal component.

Also as shown in Table 3, the transdermally absorbable preparation of Example 1 has the amount of drug permeation to the skin roughly equivalent to that of a commercially available nicotine patch, thus it is understood that the transdermally absorbable preparation of the present invention can be preferably applied to the use of a nicotine patch.

Further, as compared to Examples 34 to 38 shown in Table 7, it is understood that coloration of the adhesive layer with time was inhibited by adding BHT to the adhesive layer. Thus, it is understood that temporal stability of the transdermally absorbable preparation can be improved by adding BHT to the adhesive layer.

Example 39

After induction and drying, a mixed liquid of 53 parts by mass of the adhesive agent obtained in the above production example (a resin mixture), 42 parts by mass of nicotine (a free form) as a medicinal component, 0.2 parts by mass of lactic acid and 4.8 parts by mass of BHT was produced. The mixed liquid was applied to a nonwoven fabric, the nonwoven fabric being a backing in which unwoven fabric having a basis weight of 12 g/cm² was laminated on PET film of 12 μm thick, and was dried so that a thickness after drying would be 87 μm to form a drug retaining layer. A porous polyethylene membrane, a controlled-release membrane, (Product Name; CoTran 9719, manufactured by 3M) was pressingly arranged on a surface of the drug retaining layer. Next, to a solution of 40 parts by mass of polyisobutylene in heptane, 50 parts by mass of aliphatic hydrocarbon resin, a tackifier, (Product Name: ARKON P-100, manufactured by ARAKAWA CHEMICAL INDUSTRIES, LTD.) and liquid paraffin were added, and the obtained solution was applied to a polyester film, which was subjected to silicon treatment, and was dried so that a thickness after drying would be 67 μm to form a patching layer. The patching layer was covered with a controlled-release membrane side of the drug retaining layer obtained previously to obtain the transdermally absorbable preparation of Example 39. The cross-linking rate of the drug retaining layer in the transdermal absorbable preparation of Example 39 was evaluated by the same method as described above. The aging period taken was for one day and it was sufficiently short.

The amount of drug permeation of the transdermally absorbable preparation of Example 39 (the medicated surface area: 0.95 cm², containing 3.7 mg/cm² of nicotine) was evaluated by the same method as for the transdermally absorbable preparation of Example 1. A commercially available nicotine patch (NICODERM™, containing 5.2 mg/cm² of nicotine) punched out in the same size as the transdermally absorbable preparation of Example 39 (0.95 cm²) was used as control sample. Consequently, as shown in Table 8, cumulative amounts of nicotine eluted into a receiver at 4 hours, 8 hours and 24 hours from the onset of the test were 198 μg, 451.9 μg and 942.8 μg, respectively, per 1 cm² of the transdermally absorbable preparation. The results confirmed that a type of transdermally absorbable preparation having a controlled-release membrane of the present invention also delivered successfully a medicinal component to the skin.

Particularly, the transdermally absorbable preparation has a lower amount of drug than that of a commercially available nicotine patch, however it has the amount of drug permeation to the skin roughly equivalent to that of a commercially available product. Thus, it is understood that the transdermally absorbable preparation of the present invention can be preferably applied to the use of a nicotine patch.

TABLE 8

| | nicotine amount eluting into receiver (μg/cm²) | | |
|---|---|---|---|
| | at 4 hours | at 8 hours | at 24 hours |
| Example 39 | 198.0 ± 14.8 | 451.9 ± 18.3 | 942.8 ± 23.5 |
| control | 223.0 ± 23.0 | 511.1 ± 25.6 | 999.8 ± 25.8 |

The invention claimed is:

1. A transdermally absorbable preparation, having a backing and an adhesive layer which is placed on the backing and which contains an adhesive agent and a medicinal component,
the adhesive agent comprising a resin mixture comprising 100 parts by mass of an acrylic copolymer (A) and 0.1 to 30 parts by mass of an acrylic copolymer (B), and the adhesive layer further comprising at least one organic acid selected from lactic acid, salicylic acid, succinic acid, thioglycolic acid, maleic acid, malonic acid, adipic acid, benzoic acid, capric acid, sorbic acid, malic acid, and hydrates thereof, and the medicinal component is nicotine or lidocaine, or salts thereof;
wherein the acrylic copolymer (A) comprises a (meth) acrylic acid alkyl ester as a main monomer component, and comprises 3 to 45% by mass of diacetone acrylamide as a prerequisite monomer component, but does not comprise a free carboxyl group, and has a weight average molecular weight of 1,200,000 to 2,500,000; and
wherein the acrylic copolymer (B) comprises a (meth) acrylic acid alkyl ester as a main monomer component, and comprises a carboxyhydrazide group on side chains, but does not comprise a free carboxyl group, and has a weight average molecular weight of 2,000 to 10,000.

2. The transdermally absorbable preparation according to claim 1, wherein the adhesive layer further comprises an antioxidant.

3. The transdermally absorbable preparation according to claim 2, wherein the antioxidant is dibutylhydroxytoluene.

4. The transdermally absorbable preparation according to claim 1, further comprising a patching layer which provides a patching property for the skin or sequentially comprising a controlled-release membrane which controls release of the medicinal component from the adhesive layer and the patching layer which provides the patching property for the skin on a surface of the adhesive layer.

5. The transdermally absorbable preparation according to claim 1, wherein the medicinal component is nicotine or a salt thereof.

6. The transdermally absorbable preparation according to claim 1, wherein the acrylic copolymer (B) is a copolymer in which a dihydrazide of dicarboxy acid is reacted with an acrylic copolymer polymerized from one or more monomers including alkyl (meth)acrylate, diacetoneacrylamide, acrolein, or acetoacetoxyethyl methacrylate.

7. The transdermally absorbable preparation according to claim 6, wherein the dihydrazide of dicarboxy acid includes adipic acid dihydrazide, glutaric acid dihydrazide, or pimelic dihydrazide.

8. The transdermally absorbable preparation according to claim 1, wherein the organic acid is at least one of thioglycolic acid, malonic acid, adipic acid, sorbic acid, malic acid, and hydrates thereof.

9. A transdermally absorbable preparation, having a backing and an adhesive layer which is placed on the backing and which contains an adhesive agent and a medicinal component, the adhesive agent comprising a resin mixture comprising 100 parts by mass of an acrylic copolymer (A) and 0.1 to 30 parts by mass of an acrylic copolymer (B), and the adhesive layer further comprising 0.05 to 2% by mass of at least one organic acid selected from lactic acid, salicylic acid, succinic acid, thioglycolic acid, maleic acid, malonic acid, adipic acid, benzoic acid, capric acid, sorbic acid, malic acid, and hydrates thereof based on the total mass of the adhesive layer, and the medicinal component is nicotine or lidocaine, or salts thereof;

wherein the acrylic copolymer (A) comprises a (meth)acrylic acid alkyl ester as a main monomer component, and comprises 3 to 45% by mass of diacetone acrylamide as a prerequisite monomer component, but does not comprise a free carboxyl group, and has a weight average molecular weight of 1,200,000 to 2,500,000; and wherein the acrylic copolymer (B) comprises a (meth)acrylic acid alkyl ester as a main monomer component, and comprises a carboxyhydrazide group on side chains, but does not comprise a free carboxyl group, and has a weight average molecular weight of 2,000 to 10,000.

10. The transdermally absorbable preparation according to claim 9, wherein the medicinal component is nicotine or a salt thereof.

11. The transdermally absorbable preparation according to claim 9, wherein the adhesive layer further comprises an antioxidant.

12. The transdermally absorbable preparation according to claim 9, further comprising a patching layer which provides a patching property for the skin, or sequentially comprising a controller-release membrane which controls release of the medicinal component from the adhesive layer and the patching layer which provides the patching property for the skin on a surface of the adhesive layer.

13. The transdermally absorbable preparation according to claim 9, wherein the organic acid is at least one of thioglycolic acid, malonic acid, adipic acid, sorbic acid, malic acid, and hydrates thereof.

* * * * *